(12) United States Patent
Hamada et al.

(10) Patent No.: US 9,754,158 B2
(45) Date of Patent: Sep. 5, 2017

(54) TRAINING DEVICE

(75) Inventors: Kazuyuki Hamada, Tokyo (JP);
Takeshi Akiba, Kanagawa (JP);
Junichi Hoshino, Ibaraki (JP)

(73) Assignee: SYSTEM INSTRUMENTS CO., LTD., Tokyo (JP)

( * ) Notice: Subject to any disclaimer, the term of this patent is extended or adjusted under 35 U.S.C. 154(b) by 432 days.

(21) Appl. No.: 14/390,285

(22) PCT Filed: Sep. 6, 2012

(86) PCT No.: PCT/JP2012/072795
§ 371 (c)(1),
(2), (4) Date: Oct. 2, 2014

(87) PCT Pub. No.: WO2014/038049
PCT Pub. Date: Mar. 13, 2014

(65) Prior Publication Data
US 2015/0081057 A1 Mar. 19, 2015

(51) Int. Cl.
*G06K 9/00* (2006.01)
*A63B 23/12* (2006.01)
(Continued)

(52) U.S. Cl.
CPC ..... *G06K 9/00342* (2013.01); *A61N 1/36003* (2013.01); *A63B 21/0004* (2013.01);
(Continued)

(58) Field of Classification Search
CPC .......................... G06K 9/00342; A61N 1/36003
(Continued)

(56) References Cited

U.S. PATENT DOCUMENTS

2004/0015207 A1\* 1/2004 Barriskill ........... A61N 1/36003
607/49
2004/0023759 A1 2/2004 Duncan et al.
(Continued)

FOREIGN PATENT DOCUMENTS

CN 101961527 2/2011
JP A-7-36363 2/1995
(Continued)

OTHER PUBLICATIONS

Mar. 2, 2016 Office Action issued in Chinese Patent Application No. 201280075210.6.
(Continued)

*Primary Examiner* — Thomas Hong
(74) *Attorney, Agent, or Firm* — Oliff PLC

(57) ABSTRACT

A training device includes an information outputter, an exercise status detector, an arithmetic processor, and a stimulus signal generator. The information outputter includes at least one of an image output unit and an audio output unit. The exercise status detector includes a body portion, a first grip portion and a second grip portion provided on the body portion, and sensors that detect a motion of the body portion. The arithmetic processor issues training action instruction information through the information outputter, and evaluates a matching degree between the contents of the training action instruction information and the motion of the body portion, based on output signals from the sensors of the exercise status detector. The stimulus signal generator applies a stimulus signal to the arm of a trainee.

9 Claims, 12 Drawing Sheets

(51) Int. Cl.
*A63B 71/06* (2006.01)
*A63B 21/00* (2006.01)
*A63B 21/072* (2006.01)
*A63B 23/035* (2006.01)
*A63B 24/00* (2006.01)
*A61N 1/36* (2006.01)
*A63B 22/00* (2006.01)
*A61N 1/04* (2006.01)

(52) U.S. Cl.
CPC .... *A63B 21/00181* (2013.01); *A63B 21/0726* (2013.01); *A63B 23/03525* (2013.01); *A63B 23/12* (2013.01); *A63B 24/0006* (2013.01); *A63B 24/0087* (2013.01); *A63B 71/0622* (2013.01); *A61N 1/0452* (2013.01); *A61N 1/0456* (2013.01); *A61N 1/36014* (2013.01); *A63B 21/4035* (2015.10); *A63B 21/4043* (2015.10); *A63B 23/1209* (2013.01); *A63B 2022/0094* (2013.01); *A63B 2024/0012* (2013.01); *A63B 2024/0093* (2013.01); *A63B 2071/0625* (2013.01); *A63B 2213/004* (2013.01); *A63B 2220/16* (2013.01); *A63B 2220/34* (2013.01); *A63B 2220/40* (2013.01); *A63B 2220/51* (2013.01); *A63B 2220/89* (2013.01); *A63B 2225/15* (2013.01); *A63B 2225/50* (2013.01)

(58) Field of Classification Search
USPC .......................................................... 434/247
See application file for complete search history.

(56) References Cited

U.S. PATENT DOCUMENTS

| | | |
|---|---|---|
| 2004/0044381 A1 | 3/2004 | Duncan et al. |
| 2008/0288020 A1* | 11/2008 | Einav .................. A61N 1/36003 607/48 |
| 2009/0018612 A1 | 1/2009 | Duncan et al. |
| 2009/0030482 A1 | 1/2009 | Barriskill et al. |
| 2010/0069796 A1 | 3/2010 | Duncan et al. |
| 2011/0004126 A1* | 1/2011 | Einav .................. G06F 19/3481 600/595 |
| 2011/0077128 A1 | 3/2011 | Hamada et al. |

FOREIGN PATENT DOCUMENTS

| | | | |
|---|---|---|---|
| JP | A-8-224330 | 9/1996 | |
| JP | A-2001-321458 | 11/2001 | |
| JP | A-2004-505709 | 2/2004 | |
| JP | A-2007-209636 | 8/2007 | |
| JP | A-2009-45236 | 3/2009 | |
| JP | 2009-112791 A | 5/2009 | |
| JP | A-2011-67319 | 4/2011 | |
| JP | A-2012-65943 | 4/2012 | |
| KR | 2010-0072582 A | 7/2010 | |
| WO | 2006/121463 A2 | 11/2006 | |
| WO | WO 2006121463 A2 * | 11/2006 | ........... A61N 1/0452 |

OTHER PUBLICATIONS

Mar. 20, 2015 Office Action issued in Korean Application No. 10-2014-7030046.
Mar. 19, 2015 International Preliminary Report on Patentability issued in Application No. PCT/JP2012/072795.
Yokoi et al., "Development of Reflex Electric Stimulation Device for Assisting Walk," *Brain and Nerve*, Nov. 2010, vol. 62, No. 11 (with abstract).
International Search Report issued in International Application No. PCT/JP2012/072795 mailed Oct. 2, 2012.

* cited by examiner

TRAINING DEVICE

TECHNICAL FIELD

The present invention relates to training devices, and more particularly relates to a training device using a stimulus signal.

BACKGROUND ART

Various training devices have been known as disclosed in Japanese Patent Laid-Open No. 2009-45236 for example. When training is conducted, various training devices (training machines) are often used depending on purposes. There are a wide variety of situations where training is conducted. To accomplish various objects, training is conducted in various scenes including muscle training for healthy people and athletes, a preventive care for elderly people, or a convalescent rehabilitation.

Meanwhile, in recent years, research on induction of muscle activities by using electrical stimulation and the like is being pursued with respect to a walking assist system for persons having difficulty in walking due to disabilities, such as cranial nerve palsy. In this regard, research fields such as brain-machine interface (BMI) and neuro-rehabilitation are being active. Related technical literatures include, for example, "Development of a reflex electrical stimulation device to assist walking" by Hiroshi Yokoi, et al. in BRAIN and NERVE-Progress in research of nerve, issued on November 2010, vol. 62, No. 11 "Walking and Abnormalities" ("Hokou to Sonoijou" in Japanese). In practical applications of research achievements in such fields, training to do walking and other actions correctly (smoothly) to some extent and/or training for restoring muscle force used therefor are needed for persons with disabilities to recover to the level of being able to return to everyday life.

CITATION LIST

Patent Literature

Patent Literature 1: Japanese Patent Laid-Open No. 2009-45236
Patent Literature 2: Japanese Patent Laid-Open No. 2011-67319

SUMMARY OF INVENTION

Technical Problem

The inventor of the present invention has pursued development of the technology for trainees with disability of their one arm being paralyzed so as to restore the function of the paralyzed arm. The term "training" hereinafter includes various kinds of training such as rehabilitation training for elderly people or for convalescent care.

When a stimulus signal is applied in scenes of rehabilitation and the like, nerves, a brain, and muscles can be stimulated and training actions can be assisted thereby. Specifically, the stimulus signal is a signal generated so that a predetermined stimulus is applied to a trainee (user) with specific strength (such as voltage in the case of electrical signals) and/or specific frequency. When the stimulus signal is received, a stimulus is applied to the body (affected part) of the trainee. Training effects can be enhanced by appropriate generation and application of the stimulus signal. The inventor of the present invention has paid attention to the fact that research activities in the field of the aforementioned BMI and the like are active, and has found out a technical idea of using a stimulus signal for above-stated functional recovery of the arm.

An object of the present invention is to provide a new training device capable of effectively recovering the function of the arm by using a stimulus signal.

Solution to Problem

A training device according to a first aspect of the present invention is a training device including a information outputter, an exercise status detector, an arithmetic processor, and a stimulus signal generator.

The information outputter includes at least one of display output unit and voice output unit.

The exercise status detector includes a body portion, a first grip portion and a second grip portion provided with the body portion, and a sensor detecting a movement of the body portion.

The arithmetic processor outputs training action instruction information via the information outputter, and evaluates a degree of matching between a content of the training action instruction information and the movement of the body portion based on an output signal from the sensor.

The a stimulus signal generator can provide a stimulus signal to an arm of a trainee.

According to a second aspect of the present invention, the arithmetic processor in the first aspect stores the training action instruction information and information relating to the stimulus signal of the stimulus signal generator. The arithmetic processor calculates information relating to an adequacy degree of the stimulus signal based on the output signal from the sensor of the exercise status detector, the content of the training action instruction information, and the information relating to the stimulus signal.

This makes possible to perform a total evaluation of a training by including the adequacy degree of the stimulus signal into evaluation items.

According to a third aspect of the present invention, the arithmetic processor in the second aspect increase or decrease a next stimulus level by calculating with respect to each exercise type based on the output signal from the sensor of the exercise status detector and a target value of exercise in the content of the training action instruction information, and calculates the next stimulus level as the information relating to the adequacy degree of the stimulus signal.

This makes possible to evaluate the adequacy of the stimulus signal individually with respect to each exercise type, and to calculate a total of the evaluations for the next stimulus level.

According to a fourth aspect of the present invention, any one of the first to third aspects further includes communication means for communicating a signal between the arithmetic processor and the stimulus signal generator. The arithmetic processor generates, based on a result of evaluation of the degree of matching, signal specifying information to specify the stimulus signal that the stimulus signal generator should generate, and transmits the signal specifying information via the communication means. The stimulus signal generator generates the stimulus signal in accordance with the signal specifying information.

This makes it possible to feedback an evaluation result of the training to a control content of the stimulus signal generator.

According to a fifth aspect of the present invention, in any one of the first to fourth aspects, the sensor of the exercise status detector includes a pressure sensor, an acceleration sensor, and an angle sensor. The pressure sensor is provided with the first grip portion and the second grip portion, and detects a grip or a finger pressure when those grip portions are gripped. The acceleration sensor detects acceleration according to the movement of the body portion. The angle sensor detects a rotation angle of the body portion.

This makes it possible to implement sensing of various exercises with accuracy.

Advantageous Effects of Invention

According to the present invention, a new training device capable of effectively recovering the function of the arm by using a stimulus signal is provided.

DESCRIPTION OF EMBODIMENTS

First Embodiment

[Device Configuration According to First Embodiment]
(Component Member)

Figure 1:
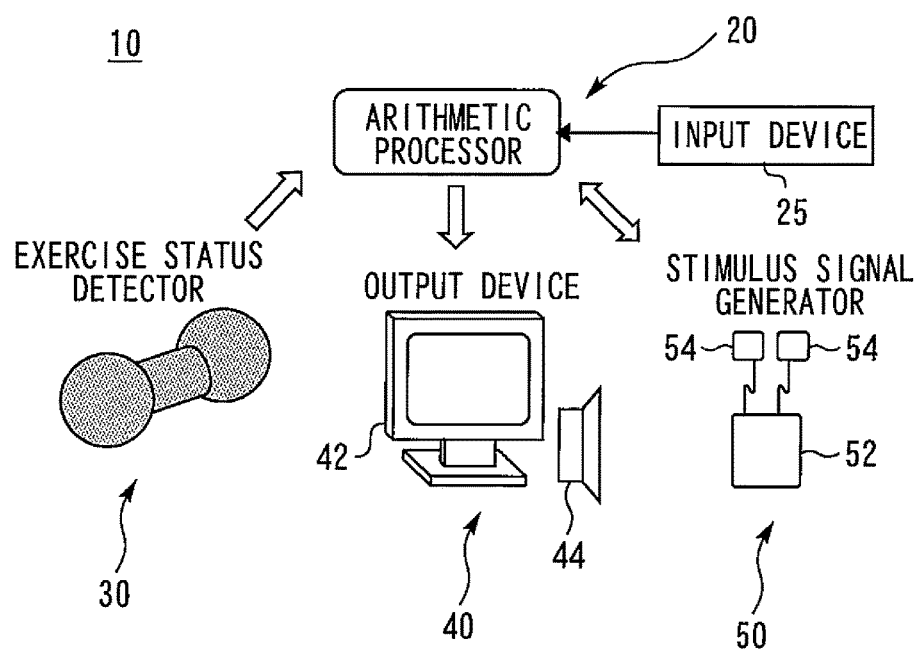
FIG. 1 is an explanatory view of the configuration of a training device according to a first embodiment of the present invention.
Figure 2:
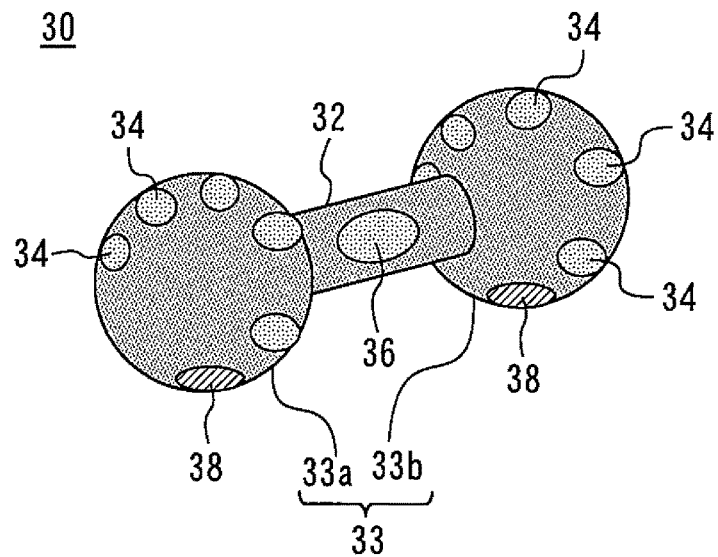
FIG. 2 is an explanatory view of the configuration of a training device according to a first embodiment of the present invention.
Figure 3:
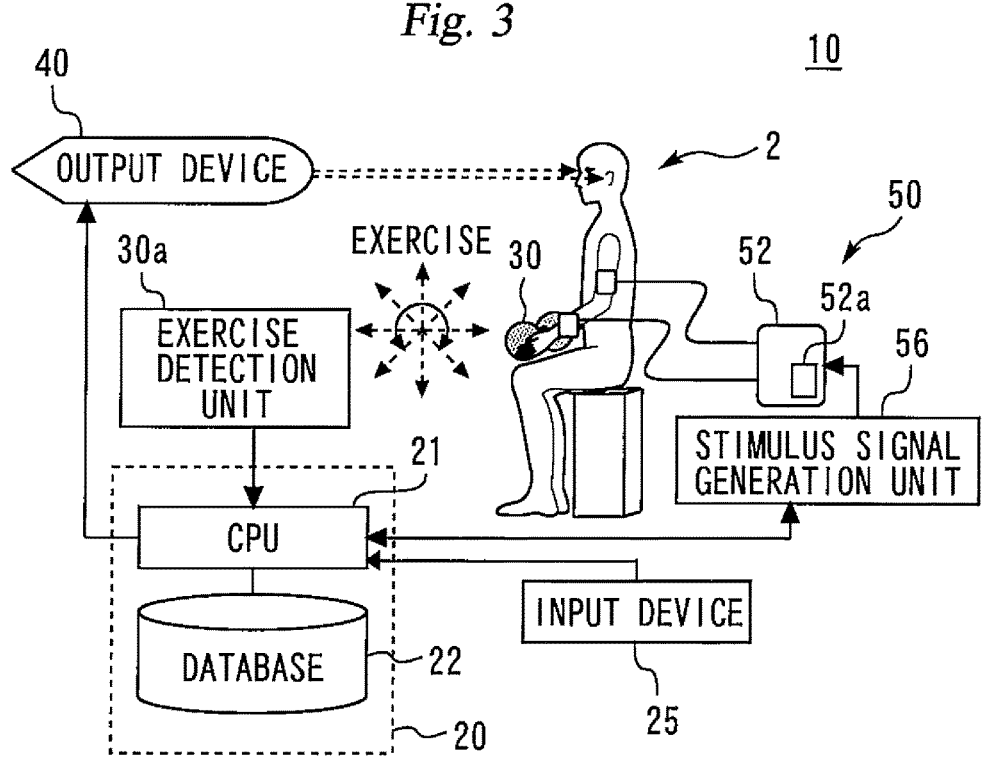
FIG. 3 is an explanatory view of the configuration of a training device according to a first embodiment of the present invention.

FIGS. 1 to 3 are explanatory views of the configuration of a training device 10 according to a first embodiment of the present invention. The training device 10 can provide a trainee, who has disability of one arm being paralyzed, with a training for restoring the function of the paralyzed arm. The trainee 2 holds an exercise status detector 30 with both hands, and conducts a training that is to move the exercise status detector 30 so as to reproduce the contents of the training action directions given through visual and auditory senses.

FIG. 1 is a concept view illustrating component members of the training device 10 according to the first embodiment. The training device 10 includes an arithmetic processor 20, an exercise status detector 30, an output device 40, and a stimulus signal generator 50.

The exercise status detector 30 is a device for detecting the exercise status of a trainee.

The output device 40 can display and voice-output the information for instructing training actions for the trainee. The output device 40 includes an image display monitor 42 made up of a liquid crystal panel and the like, and an audio output speaker 44.

The stimulus signal generator 50 can generate a stimulus signal in a stimulus signal generator body 52, and can provide the signal to the trainee through an electrode pad 54. The stimulus signal stimulates nerves, a brain, and muscles of the trainee so that the exercise of the trainee is assisted.

The arithmetic processor 20 is adapted to control the training device 10. The arithmetic processor 20 exchanges signals with the exercise status detector 30, the output device 40, and the stimulus signal generator 50. The signal exchange may be conducted by connecting each component member via a wired communication line, or by connecting each component member via a wireless communication network (LAN). The arithmetic processor 20 acquires a sensor output signal from the exercise status detector 30.

The arithmetic processor 20 is connected to an input device 25. The input device 25, which is adapted to give inputs to the training device 10 from the outside, includes input devices, such as keyboards, mouse devices, and various kinds of dial control units. The monitor 42 and the input device 25 may integrally be configured as a touch panel display and the like.

The arithmetic processor 20 executes processes to output "training action instruction information" and "evaluation result of training" to the output device 40. "The training action instruction information" is to instruct what kind of action the trainee should perform. The information is generated in advance and stored in the arithmetic processor 20. In accordance with the "training action instruction information", the arithmetic processor 20 sends a signal to the output device 40, where images and moving images are displayed and/or a voice announcement is made so that an action instruction can be provided to the trainee. The "evaluation result of training" is a result of evaluating a matching degree between the training action instruction information and an actual training action of the trainee 2 detected by using the exercise status detector 30.

(Details of Exercise Status Detector 30)

FIG. 2 is an explanatory view illustrating the configuration of the exercise status detector 30. The exercise status detector 30 is a device for detecting the exercise status of a trainee. The exercise status detector 30 has a shape like an iron dumbbell. The exercise status detector 30 includes a body portion 32 as a shaft. On opposite ends of the body portion 32, two spherical grip portions 33 are provided. One grip portion may also be referred to as a grip portion 33a while the other grip portion may be referred to as a grip portion 33b. The trainee 2 holds the exercise status detector 30 with both hands so as to wrap the grip portions 33 with his/her palms. The grip portion 33 includes a plurality of pressure sensors 34. The trainee 2 brings each of his/her fingertips of both hands into one-on-one contact with each of sensor surfaces of the pressure sensors 34. The exercise status detector 30 itself is made sufficiently lightweight. The trainee 2 can perform training actions by holding and moving the exercise status detector 30.

The exercise status detector 30 includes a plurality of kinds of sensors for exercise evaluation. The above-stated pressure sensors 34 can detect the pressure of each finger when the spherical grip portions 33 are gripped.

The body portion 32 includes a various sensors portion 36. The various sensors portion 36 includes an acceleration sensor and an angle sensor. The acceleration sensor can detect an exercise involving movement of the exercise status detector 30 in a vertical direction (up-and-down direction). The angle sensor can detect an angle and an angular velocity. Gyro sensors, geomagnetic sensors and the like may be used as the angle sensor. Accordingly, inclination of the exercise status detector 30 with respect to a horizontal direction, inclination of the exercise status detector 30 with respect to a plumb line, and rotary motion of the exercise status detector 30 can be detected.

A position sensor 38 is used to detect an exercise start position (a vertical height position to be specific). This makes it possible to detect the height directional position of the exercise status detector 30 at the start of training actions.

Since these sensors are implemented by various technologies which are not new but are publicly known, a description of their specific configurations and the like is omitted.

The exercise status detector 30 incorporates a transmitter which transmits information such as output signals from the pressure sensor 34, the various sensors portion 36, and the position sensor 38, through wireless communication.

(System Block Diagram)

FIG. 3 is a block diagram illustrating a system configuration of the training device 10. As described with reference to FIG. 1, the training device 10 includes an arithmetic processor 20, an exercise status detector 30, an output device 40, and a stimulus signal generator 50.

The arithmetic processor 20 includes a central processing unit (CPU) 21 and a database 22. The arithmetic processor 20 includes a storage (such as hard disks and memories). The database 22 is built in the storage of the arithmetic processor 20. In the first embodiment, the arithmetic processor 20 can control the stimulus signal generation by the stimulus signal generator 50. The arithmetic processor 20 also stores a program for putting "information relating to training" in a database. Specifically, the "information relating to training" includes the above-described training action instruction information, the information obtained from the sensors of the exercise status detector 30 (output signals, or physical values based on the output signals) during training, and an evaluation result of training.

The arithmetic processor 20 is connected to an exercise detection unit 30a. The exercise detection unit 30a performs exercise status detection integrally with the exercise status detector 30. The exercise detection unit 30a is provided as hardware different from the exercise status detector 30. The exercise status detector 30 includes a transmitter which transmits sensor output signal information, and the exercise detection unit 30a includes a receiver which receives the sensor output signal information. The exercise detection unit 30a can receive information, such as output signals from a sensor group (the pressure sensor 34, the various sensors portion 36, and the position sensor 38) included in the exercise status detector 30, through wireless communication. The transmitter and the receiver perform wireless communication. Since the technology for implementing the wireless communication, such as a wireless communication technology itself, is already a known technology, a further detailed description thereof is omitted. Communication may be performed not through wireless communication but through wired communication. Through the communication, the exercise status detected with the exercise status detector 30 is transmitted to the arithmetic processor 20 via the exercise detection unit 30a.

The arithmetic processor 20 is connected to the output device 40. The output device 40 outputs an image signal and an audio signal coming from the arithmetic processor 20. Consequently, the above-stated "training action instruction information" and "evaluation result of training" can be delivered to the trainee 2 through visual and auditory senses of the trainee 2.

The stimulus signal generator 50 includes the stimulus signal generator body 52, which is connected to the electrode pad 54. As illustrated in FIG. 3, the electrode pad 54 is attached to one arm of the trainee 2 in the present embodiment. A stimulus signal generated by the stimulus signal generator 50 is given to the one arm of the trainee 2 through the electrode pad 54.

The stimulus signal generator 50 includes a stimulus signal generation unit 56. In the present embodiment, the stimulus signal generation unit 56 is provided as hardware independent of the stimulus signal generator body 52. A control signal is provided from the stimulus signal generation unit 56 to the stimulus signal generator body 52. The stimulus signal generation unit 56 may be provided as a program installed in the arithmetic processor 20. In this case, the arithmetic processor 20 and the stimulus signal generator body 52 may directly be connected to transfer information (signals) therebetween.

The stimulus signal generation unit 56 includes a database unit built in a storage (memory) inside the stimulus signal generation unit 56. In accordance with the data stored in the database unit, an electrical signal having a voltage and a frequency specified by the data can be generated and be outputted to the electrode pad 54. The database unit stores stimulus signal parameters serving as conditions to be used when the stimulus signal generator body 52 generates a plurality of different stimulus signals. The stimulus signal parameters include an amplitude, a frequency, a burst frequency, a duty ratio, a carrier frequency, and a pattern. The database unit stores these information pieces in the form of a database in the database unit. The burst frequency is the frequency of a burst wave which is a signal that activates a portion of the brain for use in a specific exercise (action). The carrier frequency is the frequency of a carrier wave which is a signal constituted of only a carrier wave that carries no data. A carrier signal is formed of a square wave whose frequency is higher than the frequency of the burst signal. A wave formed by superimposing the burst wave and the carrier wave can be used as a stimulus signal. The strength of stimulation can be adjusted with the duty ratio. The stimulus signal generator body 52 can use information on the stimulus signal parameters from the database unit as input values. In accordance with the input values, the stimulus signal generator body 52 can output to the electrode pad 54 a plurality of kinds of stimulus signals different in voltage and/or frequency or the like.

The stimulus signal generator body 52 includes an operation unit 52a which enables manual operation. The operation unit 52a enables manual regulation of stimulus signals other than automatic regulation control by the stimulus signal generation unit 56. By operating a manual operation button provided on the operation unit 52a, the above-described stimulus signal parameters can be regulated, and/or preset stimulus signal patterns can be selected. The strength of the above-described stimulus signals, or voltage levels thereof to be precise, can be adjusted.

[Device Operation According to First Embodiment]

FIGS. 4 to 8 are explanatory views illustrating the operation of the training device according to the first embodiment of the present invention.

(Training Preparation)

Figure 4:
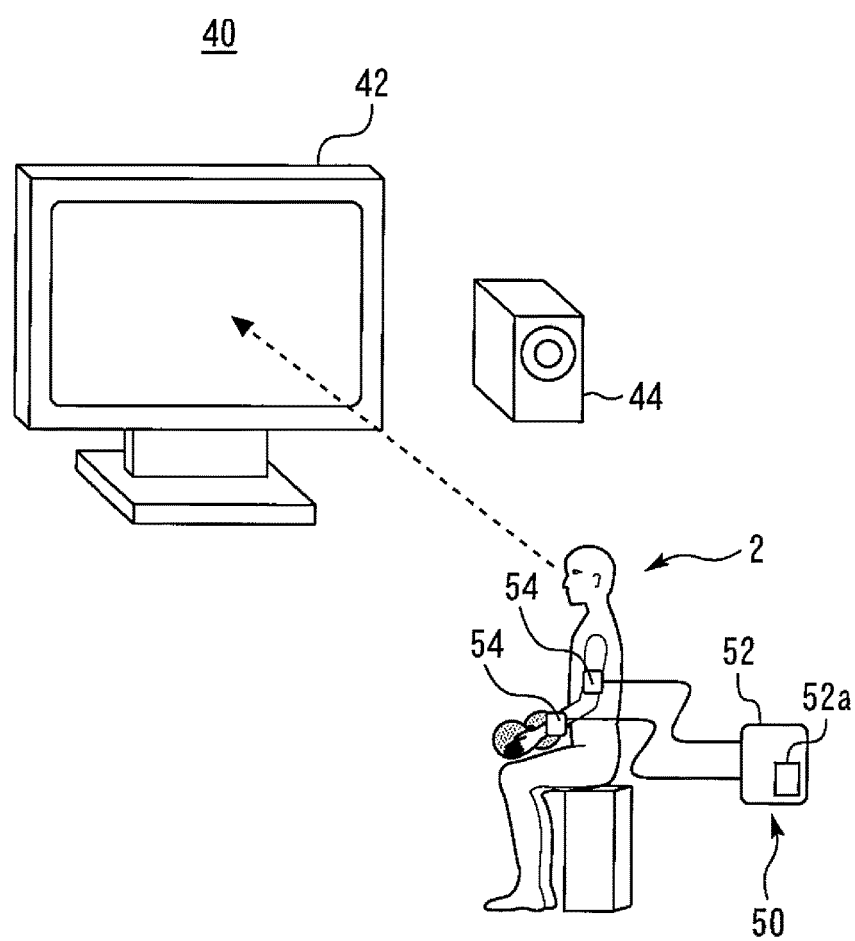
FIG. 4 is an explanatory view illustrating the operation of a training device according to a first embodiment of the present invention.

FIG. 4 illustrates a preparatory stage to conduct training. Preparation is made to conduct training as shown below.

- Perform training by holding the exercise status detector with both hands. Operating the training with both hands brings about an effect of the healthy arm guiding the exercise of the other paralyzed arm.
- Hold the exercise status detector 30 so that all the fingers touch the pressure sensors 34.
- Attach the electrode pad 54 to the paralyzed arm of the trainee 2.
- Set the exercise status detector 30 at a prescribed height position (start position) with the position sensor 38 of the exercise status detector 30. In the present embodiment, the start position of the exercise status detector 30 is set to be on the knee of the trainee 2 as a default.
- Set the trainee 2 in the state of being able to see an image on the monitor 42. The monitor 42 needs to be in a standby state. The standby state is the state in which the monitor 42 is turned on, the arithmetic processor 20 can transfer an image signal to the monitor 42, and an image can be displayed on the monitor 42 based on the image signal.
- Set the trainee 2 in the state of being able to hear sounds from a speaker 44. In other words, as in the case of the monitor 42, the speaker 44 also needs to be in a standby state in which sounds can be outputted.

When all of these conditions are right, implementation of the training is regarded to be ready.

(Details of Training Actions)

FIGS. 5 to 8 are explanatory views illustrating the training actions with use of the training device according to the first embodiment of the present invention. The stimulus signal generator 50 applies a stimulus signal to one arm of the trainee 2. In this state, while holding the exercise status detector 30, the trainee 2 performs an exercise involving movement of both arms in vertical or horizontal directions or oblique directions as viewed from the trainee 2 and/or rotation of the exercise status detector 30.

Figure 5:
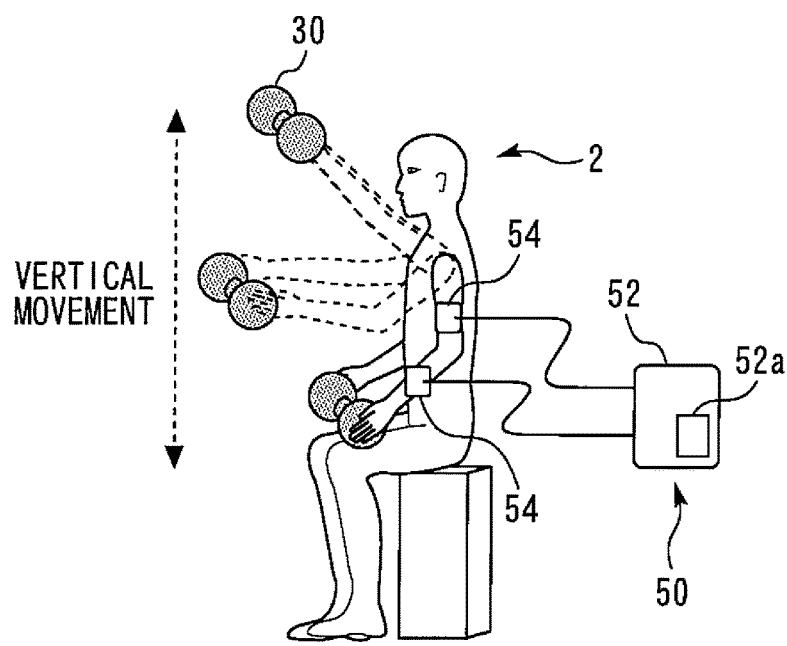
FIG. 5 is an explanatory view illustrating the operation of a training device according to a first embodiment of the present invention.

Illustrated in FIG. 5 is a training action of moving the exercise status detector 30 in the vertical direction.

Figure 6:
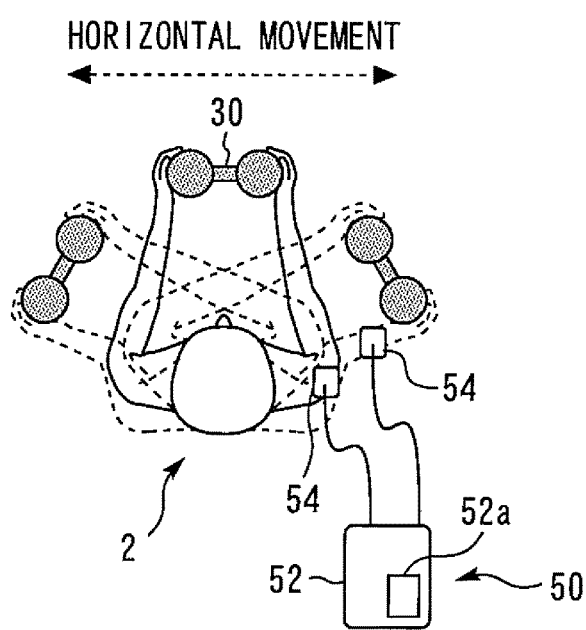
FIG. 6 is an explanatory view illustrating the operation of a training device according to a first embodiment of the present invention.

Illustrated in FIG. 6 is a training action of moving the exercise status detector 30 in the horizontal direction.

Figure 7:
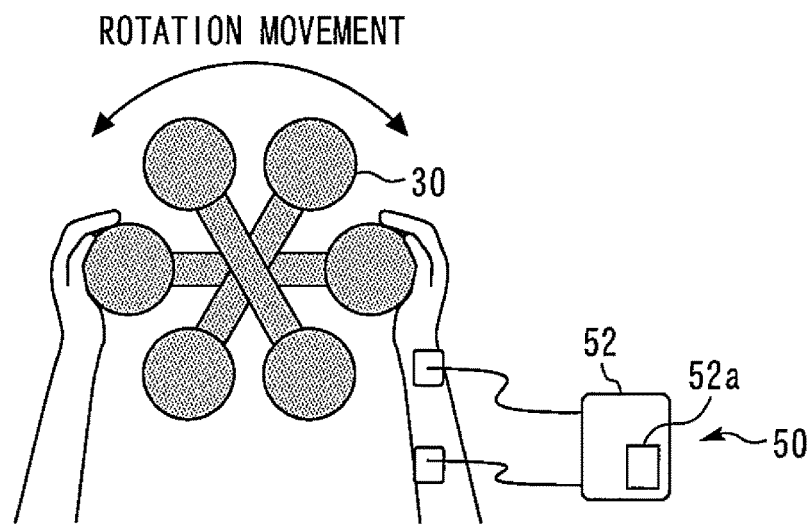
FIG. 7 is an explanatory view illustrating the operation of a training device according to a first embodiment of the present invention.

Illustrated in FIG. 7 is a training action of rotating the exercise status detector 30.

Figure 8:
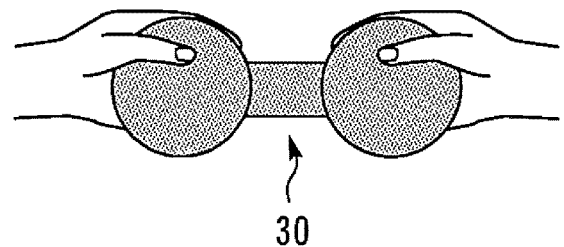
FIG. 8 is an explanatory view illustrating the operation of a training device according to a first embodiment of the present invention.

Illustrated in FIG. 8 is an exercise of grasping the exercise status detector 30, and more specifically a training action of applying pressure to the pressure sensor 34 with the fingers.

The exercises in the directions illustrated in FIGS. 5 and 6 may be combined to form a training action of moving the exercise status detector 30 in oblique directions (upper right, lower left, upper left, and lower right directions as viewed from the trainee 2). A plurality of training actions stated herein may further be combined. For example, the training action of grasping may be combined with the training action of moving, and/or the training action of rotating may be combined with the training action of moving. Since the exercise status detector 30 according to the present embodiment has a plurality of sensors as mentioned above, diverse exercises can be sensed with high accuracy. Accordingly, training actions complicated to some extent as described above can also be sensed with high accuracy.

For these exercises, not only the direction is instructed, but also extensive activity details including a moving distance, an angle of rotation, an action speed, and an acceleration in each action are specified.

(Training Action Instruction)

A plurality of the exercises in FIGS. 5 to 8 are combined and are made to be performed in a predetermined order. Accordingly, "training action instruction information" indicating the details and the order of the exercises in FIGS. 5 to 8 is stored in the database 22. By using combinations and orders of the exercises in FIGS. 5 to 8 or combinations of moving distances and/or directions, the "training action instruction information" is formed and stored in a plurality of patterns. The "training action instruction information" is displayed and outputted from the output device 40 in the form of images and sounds, so that the trainee 2 is notified of training instructions with use of moving images, illustrations, and sounds. A moving image of training actions may be photographed as an example, and this moving image may be displayed. Images and sounds in the moving image preferably may be enjoyable and encouraging for the trainee 2.

(Training Evaluation)

As the trainee 2 performs exercises while holding the exercise status detector 30, information such as output signals from the sensor group (the pressure sensor 34, the various sensors portion 36, and the position sensor 38) of the exercise status detector 30 is sequentially delivered to the exercise detection unit 30a. The output signal information is inputted into the arithmetic processor 20 from the exercise detection unit 30a. Based on this output signal information, the arithmetic processor 20 executes "training evaluation program" for evaluating the training status of the trainee 2. The arithmetic processor 20 controls the output device 40 so that "evaluation result of training" obtained from the result of executing the program is displayed as images or outputted as sounds by using numerical values, graphs, symbols, languages and the like.

The "training evaluation program" is a program of evaluating a matching degree between the training action instruction information and an actual training action of the trainee 2 detected by using the exercise status detector 30.

The "matching degree" can be evaluated based on various criteria. For example, the matching degree can be evaluated from the following viewpoints.

Criterion 1: a matching degree between a direction instructed by the training action instruction information and a direction in which the exercise status detector 30 is actually moved ("direction" herein includes a vertical direction, a horizontal direction, and a rotation direction)

Criterion 2: a matching degree between an action distance instructed by the training action instruction information and a distance that the exercise status detector 30 is actually moved ("distance" herein includes not only a moving distance in the vertical direction and the horizontal direction but a rotated angle and the number of rotations)

Criterion 3: a matching degree between a speed instructed by the training action instruction information and a speed at which the exercise status detector 30 is actually moved ("speed" herein includes not only a moving speed in the vertical and horizontal directions but also a rotating speed)

Criterion 4: a matching degree between an acceleration instructed by the training action instruction information and an acceleration when the exercise status detector 30 is actually moved ("acceleration" herein includes not only an acceleration in vertical and horizontal movements but also an angular acceleration in rotating actions)

Criterion 5: a matching degree between a grip value instructed by the training action instruction information and a grip value based on an output value of the pressure sensor 34

Criterion 6: whether a training action is smooth or not may be added as a criterion.

The "training evaluation program" grades the training results based on each of the criteria 1 to 5. As obtained values are more deviated from the parameters such as the direction in the training action instruction information, the training evaluation becomes lower. The arithmetic processor 20 notifies the trainee 2 of the grades themselves and/or evaluated levels (good, fair, poor) obtained from the grades through the output device 40 by using moving images, illustrations, and sounds.

(Storing Data in Database)

The arithmetic processor 20 executes "storing program" for storing and accumulating the information obtained during training in the database 22. The "storing program" is adapted to store in the database 22, information (output signals or physical values based on the signals) obtained from the sensors of the exercise status detector 30 during training, and/or training evaluation results based on the information of each trainee (of each user ID to be precise).

The information is stored not by overwriting each data but serially accumulating the data per training execution date. As a result, a training history can be checked. Based on the training history, training effects of each trainee can be examined, and/or various kinds of analyses involving statistical calculation can be conducted by using a plurality of information pieces.

(Processes by Arithmetic Processor 20)

Processes executed by the arithmetic processor 20 are summarized as shown below:

Read the information in the database 22 and determine training details.

Acquire output signals from the sensor group (the pressure sensor 34, the various sensors portion 36, and the position sensor 38) included in the exercise status detector 30 from the exercise detection unit 30a.

Display on the output device 40 training action instruction information matched with the determined training details.

Evaluate the training by executing the above-described training evaluation program.

Output a training evaluation result through the output device 40.

Record "information relating to training" on the database 22.

Control the stimulus signal generator 50 to adjust a stimulus signal. In this process, the training evaluation result is referred and if the training evaluation result is poor, the strength of the stimulus signal and the like is increased so as to intensify the stimulus to be applied.

[Specific Process to be Executed by Device According to First Embodiment]

Figure 9:
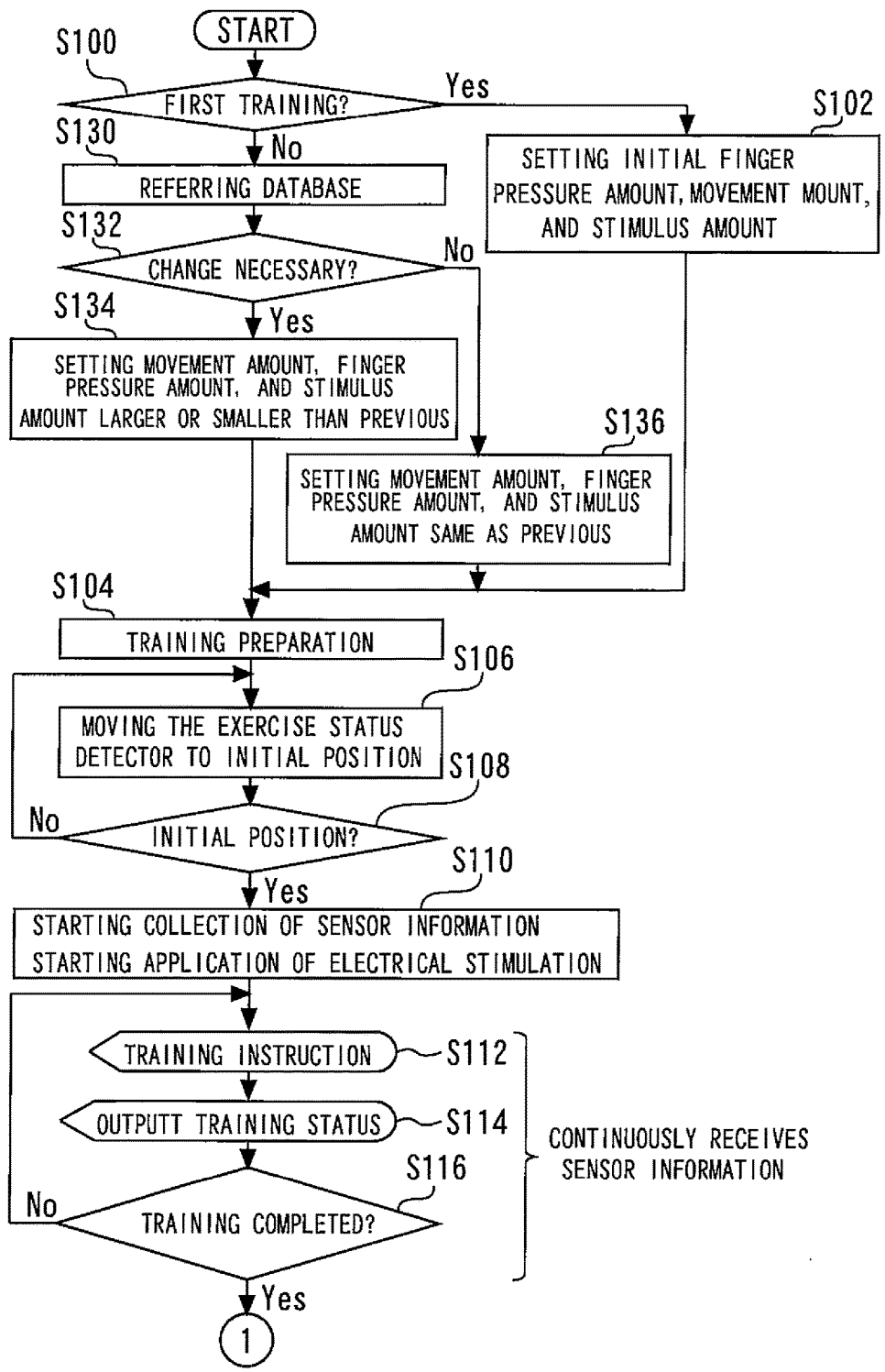
FIG. 9 is a flow chart of a routine executed by the arithmetic processor in a first embodiment of the present invention.
Figure 10:
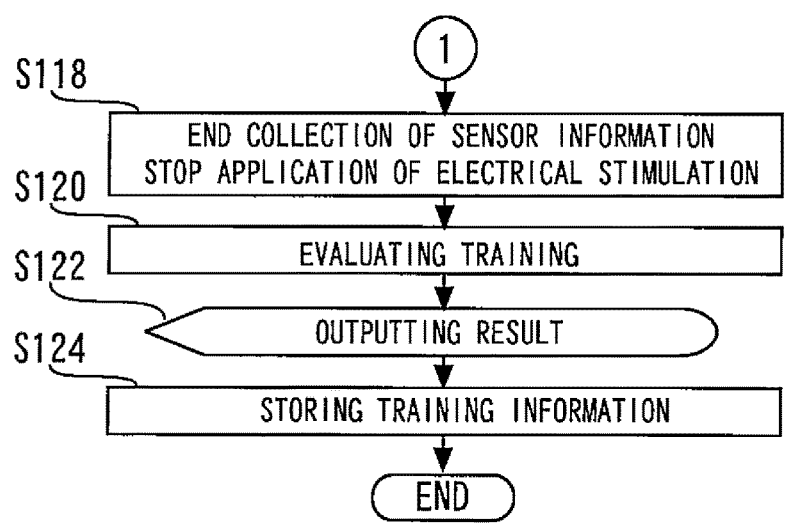
FIG. 10 is a flow chart of a routine executed by the arithmetic processor in a first embodiment of the present invention.

FIGS. 9 and 10 are flow charts of a routine executed by the arithmetic processor 20 in the first embodiment of the present invention.

In this routine, the arithmetic processor 20 first executes a process of determining whether or not a current training is the first training (Step S100). Specifically, a process of determining whether or not the user ID of a current trainee is registered in the database 22 is executed in this step. If the user ID is not registered, the current training is determined to be the first training. If the user ID is already registered but the training history of the user is not present, the current training is still determined to be the first training.

When the current training is determined to be the first training (if Yes) in step S100, the arithmetic processor 20 executes a process of setting an initial finger pressure amount, a movement mount, and a stimulus amount (step S102). In this step, since it is the first training, default values stored in the database 22 are used. The default values include a reference finger pressure amount, a reference movement amount, and a target stimulus amount. The movement amount herein include a value of "one-directional moving distance" and a value of "total movement amount (integrated movement amount) when one training is conducted".

The arithmetic processor 20 issues a training action instruction in the future so that the movement amount and the like set herein are achieved. In training evaluation, the movement amount and the like set herein are used as reference values to evaluate the training.

Next, the arithmetic processor 20 executes a training preparation process (step S104). In this step, a process of outputting to the output device 40 a guidance image and a guidance sound for encouraging the trainee 2 to make the above-stated training preparation. The guidance image and guidance sound are prepared in advance and are stored in a part of the databases 22.

Next, the arithmetic processor 20 executes a process of moving the exercise status detector 30 to an initial position (step S106). In this step, the output device 40 is made to input a message like "please move exercise status detector to initial position" with images and/or sounds based on the same concept as in the process of the above-described step S104.

Next, the arithmetic processor 20 executes a process of determining whether or not a condition regarding the initial position is satisfied (step S108). In this step, based on an output of the position sensor 38 of the exercise status detector 30, it is determined whether or not the exercise status detector 30 is stationed on the knee of the trainee 2. Whether or not the exercise status detector 3 is on the knee of the trainee 2 may be determined by registering knee position information of each trainee. Or it may be determined based on whether or not the exercise status detector 30 is stationed at a specific position determined by a relation relative to the height of a chair on which the trainee 2 sits down. When the condition of step S108 is not satisfied, the process returns to step S106. During this period, the exercise detection unit 30*a* continuously receives outputs from the sensor group of the exercise status detector 30.

When the condition of step S108 is satisfied (the detector is at the initial position), then the arithmetic processor 20 executes a process of starting collection of sensor information and also starting application of electrical stimulation (step S110). In this step, exchange of radio signals between the exercise status detector 30 and the exercise detection unit 30*a* is started, and information such as the output signals from the sensor group (the pressure sensor 34, the various sensors portion 36, the position sensor 38) included in the exercise status detector 30 is transferred to the exercise detection unit 30*a*. The application of stimulus signals by the stimulus signal generator 50 is also started. Specifically, the stimulus signal generation unit 56 controls the stimulus signal generator body 52 to start the output of stimulus signals.

Next, the arithmetic processor 20 executes a process of issuing a training instruction (step S112). In this step, a moving image and the like to instruct training actions is outputted to the output device 40 in accordance with the "training action instruction information" as described in the foregoing. The contents of the training action instruction information which should be outputted in this step are made to match with the reference finger pressure amount and the reference movement amount set in step S102.

Next, the arithmetic processor 20 executes a process of outputting a training status (step S114). In this step, a current action status of the trainee 2 is outputted as an image based on the output signals from the sensor group (the pressure sensor 34, the various sensors portion 36, the position sensor 38) included in the exercise status detector 30. The outputted image may represent the action status of the trainee 2 (such as a position, an angle and a speed of the exercise status detector 30) in the form of numerical values.

Next, the arithmetic processor 20 executes a process of determining whether or not the training is completed (step S116). In this step, it is determined whether or not all the exercise programs planned based on the training action instruction information have been completed. Specifically, it may be determined whether or not replay of the training action instruction information has finished, and/or it may be determined whether or not the trainee 2 has completed the exercise in accordance with the training action instruction information. The process returns to step S112 until the condition of this step is satisfied.

When the condition of step S116 is satisfied, the process continuously moves to step S118 in a flow chart illustrated in FIG. 10. In this step, the arithmetic processor 20 ends collection of sensor information and stops application of electrical stimulation.

Next, the arithmetic processor 20 executes a process of evaluating the training (step S120). In this step, the arithmetic processor 20 executes the aforementioned "training evaluation program."

Next, the arithmetic processor 20 executes a process of outputting the result (step S122). In this step, the arithmetic processor 20 makes the output device 40 output a training evaluation result calculated based on the training evaluation program in a predetermined format.

The arithmetic processor 20 then executes a process of storing the training information (step S124). In this step, the aforementioned "storing program" is executed.

Then, the current routine is ended.

On the contrary, if it is determined in the first step of S100 that the current training is not the first training, then the arithmetic processor 20 executes a process of referring to the database 22 (step S130). In this step, the training history in the database 22 is referred and a previous training evaluation result is read out.

Next, the arithmetic processor 20 executes a process of determining whether or not the training details need to be changed (step S132). In this step, if the previous training evaluation result is "good" or "fair", status quo is determined (i.e., it is determined that change is not necessary). If the previous training evaluation result is "poor", it is determined that change is necessary.

If it is determined that change is necessary in step S132, the arithmetic processors 20 executes a process of setting the movement amount, the finger pressure amount, and the stimulus amount to be larger or smaller than the previous amounts (step S134). In this step, the training history in the database 22 is referred, and the movement amount, the finger pressure amount, and the stimulus amount, which were set at the time of conducting the previous training, are corrected (predetermined increments are added or predetermined decrements are subtracted). A Corrected movement amount, a corrected finger pressure amount, and a corrected stimulus amount obtained by addition or subtraction are used for the current training.

To determine the correction content (addition of predetermined increments, or subtraction of predetermined decrements), conditions may be predefined so as to select either addition or subtraction based on the tendency of the evaluation results.

The process then proceeds to step S104, and the steps subsequent to step S104 are executed in a similar manner as described before.

If it is determined that change is unnecessary in step S132, the arithmetic processor 20 executes a process of setting the movement amount, the finger pressure amount, and the stimulus amount to be identical to those set in the previous training (step S136). Then, the process proceeds to step S104, and the steps subsequent to step S104 are executed in a similar manner as described before.

Modified Example of First Embodiment

In the above-described flow chart of FIG. 9, the training evaluation is performed by each of the above-described analyzing methods (step S120), and the evaluation result is used for controlling the actual movement amount and the like in the next training as described in steps S130, S132, S134, and S136. The evaluation result is used in such a way that in steps S132, if the previous training evaluation result is "good" or "fair," the status quo is determined (i.e., it is determined that change is not necessary) and if the previous training evaluation result is "poor", it is determined that change is necessary. In the first embodiment, the movement amount and the like are automatically changed (increased or decreased in conformity to a prescribed rule) based on the training evaluation result when the movement amount and the like are set at the start of the next training. The mode of automatically changing the movement amount and the like may also be referred to as "automatic movement amount and the like control mode." However, the present invention is not limited to this mode.

The training device 10 does not need to automatically adjust the movement amount and the like. More specifically, the evaluation result obtained in the above-described training evaluation may limitedly be used in such a way that the analysis result is outputted by the output device 40 or is reflected upon the process of calculating movement amount and the like setting values serving as candidate values to be set as the movement amount and the like.

By displaying the evaluation result, a determination regarding what kind of measure to take against the evaluation result, that is, for example, a final determination regarding whether or not to maintain, increase, or decrease the movement amount and the like, may be made by a trainer and the like, and/or the trainee 2 him/herself. The trainer and the like herein include a rehabilitation trainer and a medical worker who has a role of monitoring and supervising the training. Whether or not to use the movement amount and the like setting values calculated as candidate values may arbitrarily be determined by the trainer and the like, and/or the trainees 2. The trainer and the like or the trainee 2 may input, with the input unit and/or the operation unit 52a, his/her decision regarding whether or not to accept the movement amount and the like setting values (changed movement amount and the like) set based on the determination result. This is a kind of questionnaire.

Even in such a questionnaire mode, the function of evaluating the degree of adequacy of the movement amount and the like can be implemented by conducting the training evaluation. As a result, it becomes possible to reduce the load of the trainer and the like and to objectively determine the validity of regulation of the movement amount and the like with a less load and high accuracy.

The evaluation result may be displayed on the monitor 42 with use of alphabetic characters such as "proper", "hard" and "easy". The arithmetic processor 20 executes a process of displaying on the monitor 42 the alphabetic characters "proper" when it has been determined that the movement amount and the like are adequate, "hard" when it has been determined that the movement amount and the like should be reduced, and "easy" when it has been determined that the movement amount and the like should be increased.

The operation modes "automatic movement amount and the like control mode" and "questionnaire mode" used to operate the training device 10 may be switched manually or automatically. The evaluation result can be displayed even in the mode of automatically adjusting the movements amount and the like.

Second Embodiment

Figure 11:
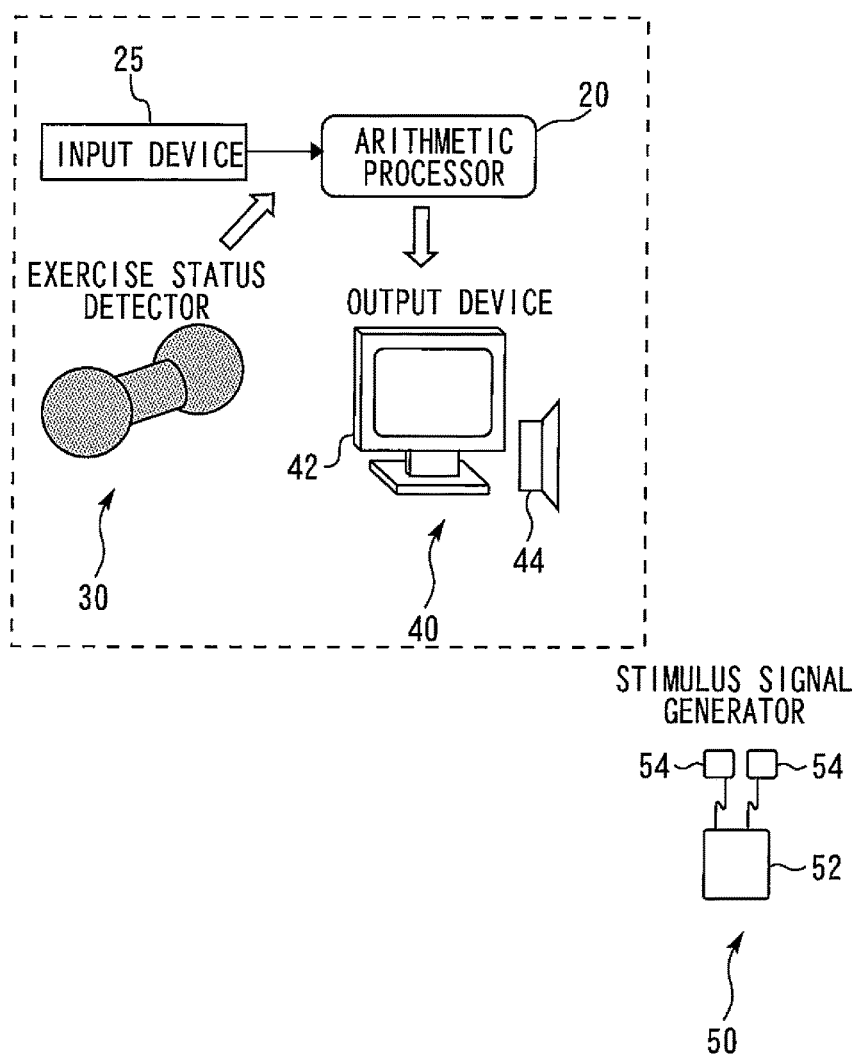
FIG. 11 is an explanatory view of the configuration of a training device 210 according to a second embodiment of the present invention.
Figure 12:
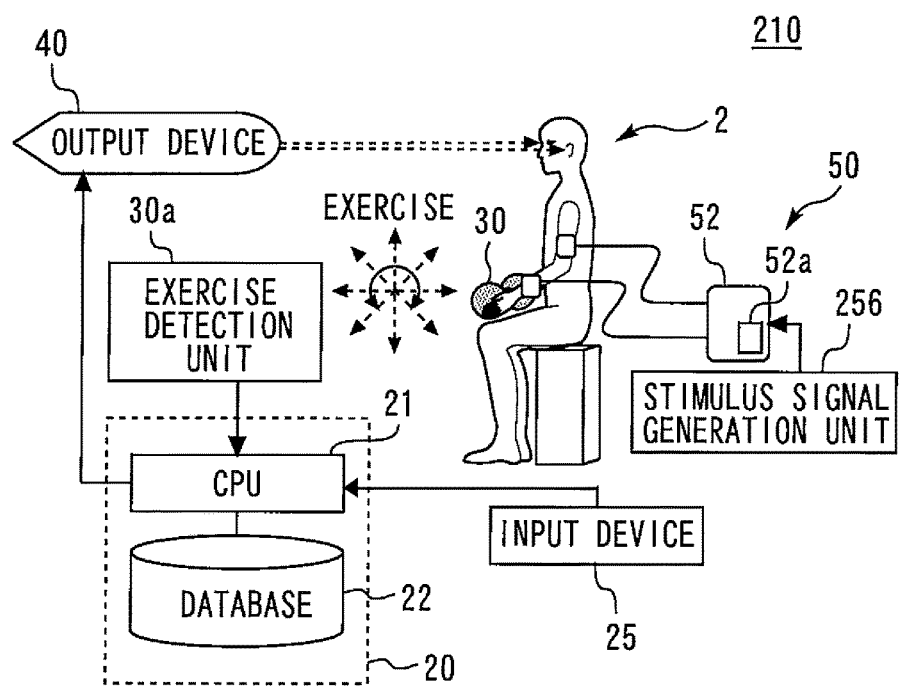
FIG. 12 is an explanatory view of the configuration of a training device 210 according to a second embodiment of the present invention.

FIGS. 11 and 12 are explanatory views of the configuration of a training device 210 according to a second embodiment of the present invention. The training device 210 is different from the training device 10 according to the first embodiment in the point that the stimulus signal generator 50 is not connected to components enclosed with a broken line in FIG. 11 (the arithmetic processor 20, the exercise status detector 30, and the output device 40). In short, the training device 210 is configured so that signal exchange is not performed between the arithmetic processor 20 and the stimulus signal generator 50.

As is clear from a block diagram of FIG. 12, a stimulus signal generation unit 256, unlike the stimulus signal generation unit 56 according to the first embodiment, is not connected to the arithmetic processor 20. The stimulus signal generation unit 256 provides the stimulus signal generator body 52 with the information relating to generation of a stimulus signal in accordance with an operation instruction from the operation unit 52a. The stimulus signal generator body 52 generates the stimulus signal.

Figure 13:
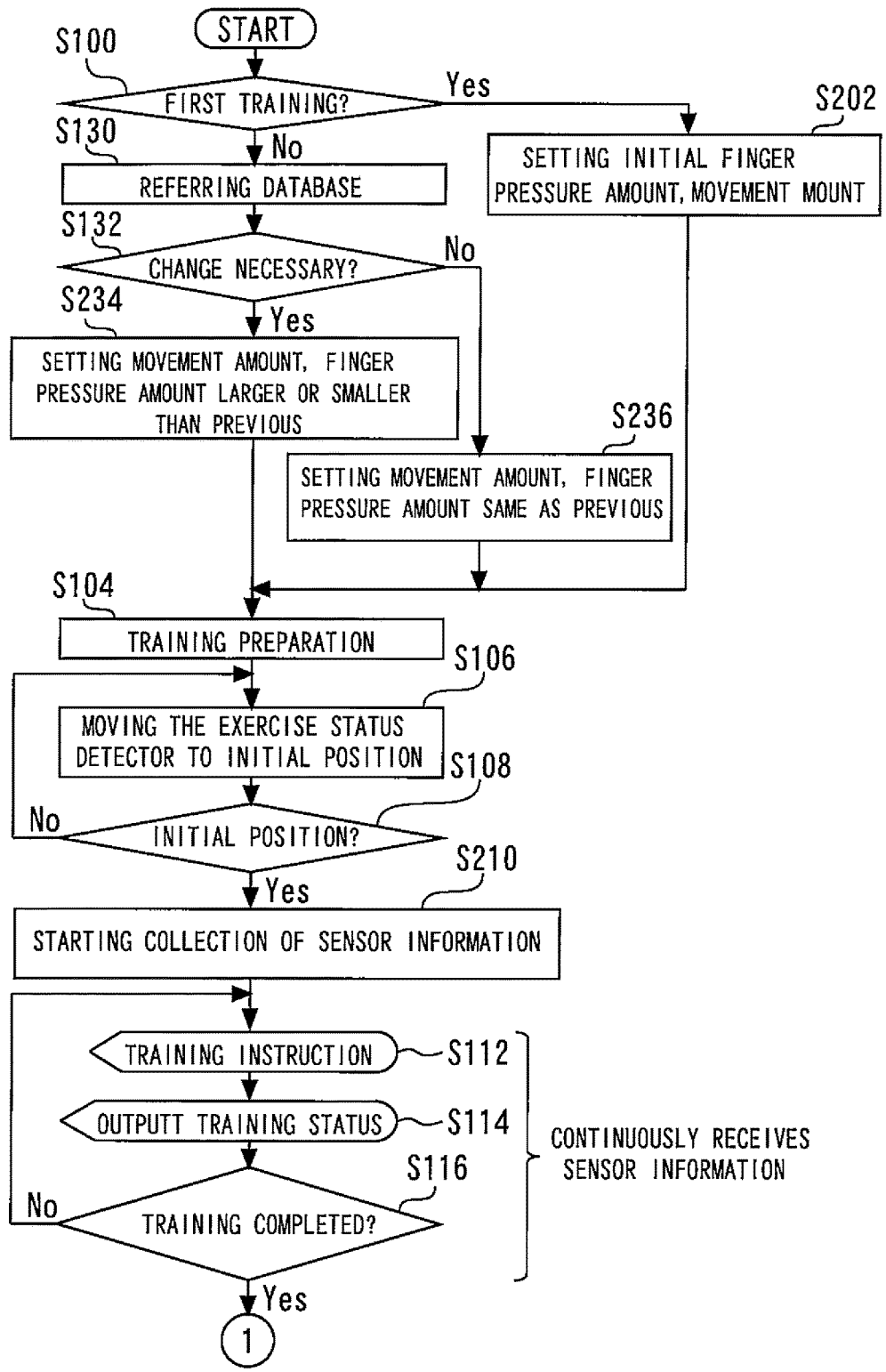
FIG. 13 is a flow chart of a routine executed by the arithmetic processor in a second embodiment of the present invention.
Figure 14:
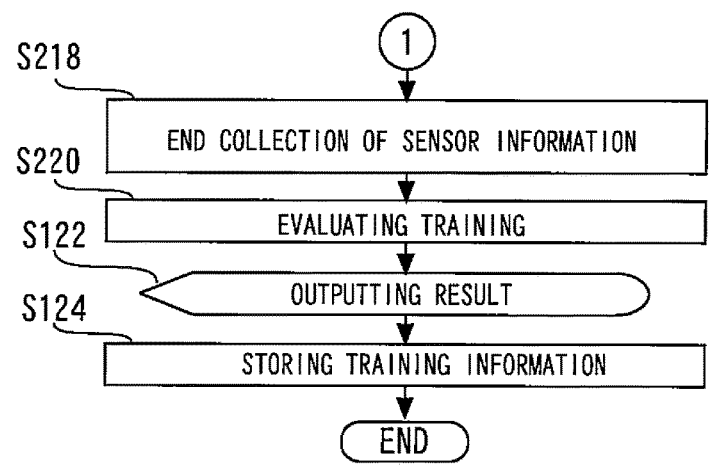
FIG. 14 is a flow chart of a routine executed by the arithmetic processor in a second embodiment of the present invention.

FIGS. 13 and 14 are flow charts of a routine executed by the arithmetic processor 20 in the second embodiment of the present invention.

In the flow chart of FIG. 13, the processing contents of the steps are similar to those in the flowchart of FIG. 9 except the steps S202, S234, S235, S210, and S218. As described in the foregoing, in the second embodiment, communication is not performed between the arithmetic processor 20 and the stimulus signal generator 50, and the arithmetic processor 20 does not control the stimulus signal generator 50. Therefore, in the second embodiment, the process with respect to the stimulus signal is not included in the flow chart executed by the arithmetic processor 20. Specifically, as compared with the routine of FIGS. 9 and 10 in the first embodiment, the process of specifying the stimulus amount is not included in steps S202, S234, and S235. The process of starting and ending application of electrical stimulation is not included in steps S210 and S218.

In the flow chart of FIG. 14, the processing contents of the steps are similar to those in the flowchart of FIG. 10 except the step 220. In step S220, the arithmetic processor 20 performs training evaluation based on output signals from the sensors of the exercise status detector 30, and the contents of the training action instruction information and the information relating to the stimulus signal in the database 22.

A description is herein given of what kind of "information relating to the stimulus signal" is stored in the database 22 in the second embodiment. Amplitudes representing the strength of stimulation, stimulus signal frequencies (duty ratios of both the carrier wave and the burst wave), and stimulation application patterns (combinations of the amplitudes and the frequencies, their time-series changes, and the like) are stored in the database 22 as "information relating to the stimulus signal." The information is manually stored (saved) in the database 22 by using the input device 25. Accordingly, even in the case where the stimulus signal generator 50 is not included in a training system, the information relating to the stimulus signal is manually inputted, so that training evaluation can be conducted in consideration of the relation between stimulation and an exercise amount. In conducting the training, a target position, a target speed, and the like are set as an exercise target, and a difference between an actual exercise amount and a target value is evaluated. The training is evaluated by using information on the evaluation result and the stimulus signal. This makes it possible to make an accurate and stable determination regarding whether or not the strength of stimulation applied by the stimulus signal generator 50 is proper.

(Evaluation Process in Step S200)

Figure 15:
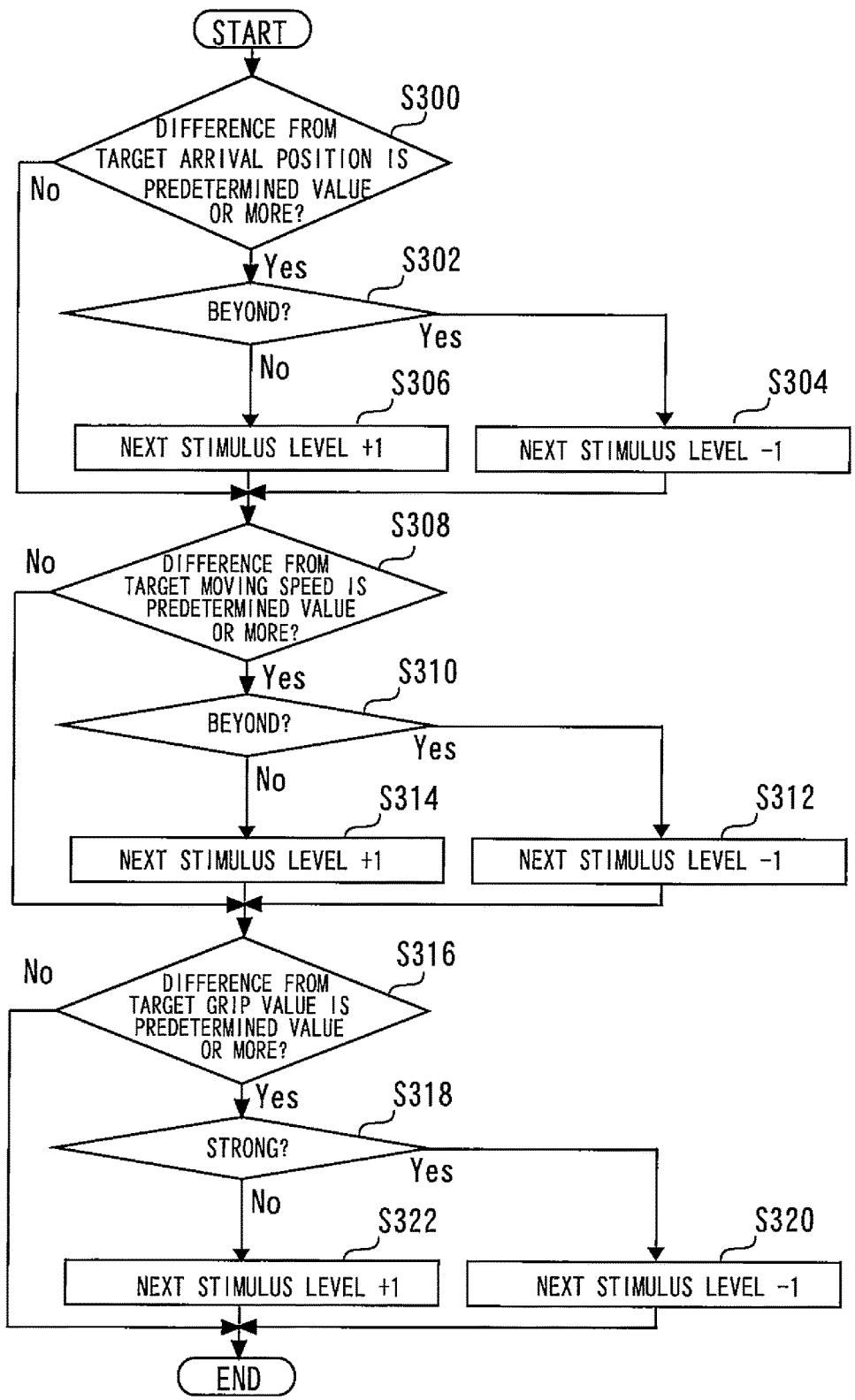
FIG. 15 is a flow chart of a routine executed by the arithmetic processor in a second embodiment of the present invention.

FIG. 15 is a flow chart illustrating a part of the contents of the process (the part regarding stimulus signal evaluation) in step S220 in the flowchart of FIG. 14.

In the routine illustrated in FIG. 15, the arithmetic processor 20 first executes a process of determining whether or not a difference between an exercise arrival position detected with the exercise status detector 30 and a predetermined target arrival position is equal to or larger than a predetermined value (step S300). The predetermined target arrival position is a position determined on a coordinate system having an initial position when the trainee 2 holds the exercise status detector 30 (step S108) as an origin. This predetermined target arrival position is a value determined by the "action distance instructed by the training action instruction information" in the criterion 2 in the "training evaluation program" with the origin as a reference. As the coordinate system, a one-dimensional, two-dimensional, or three-dimensional coordinate system may be selected as necessary. One piece of the "training action instruction information" may include this predetermined target arrival position. The predetermined value (determination value) to be used for determination in this step is specified on the basis of whether or not the value is large enough to be used to determine that a difference from the target position is significant, i.e., whether or not a difference from the target position is in an allowable range.

When the determination result in step S300 is affirmative (Yes), then the arithmetic processor 20 executes a process of determining whether or not the "difference from the target position" detected in step S300 is beyond a set value with the target position as a reference (step S302). In this step, it can be determined whether or not the exercise status detector 30 moves too much (moves beyond the target position) with the target position as a reference.

When the determination result of step S302 is affirmative (Yes), the arithmetic processor 20 decrements a next stimulus level from the current level by 1 (step S304). The "next stimulus level" is a value used as an index to set the strength of the stimulus signal and the like for the next training. If the determination result in step S302 is affirmative (Yes), the result can lead to the conclusion that the stimulus level by the stimulus signal is too high and the stimulus level applied to the trainee 2 is higher than a proper level.

If the determination result of step S302 is negative (No), the arithmetic processor 20 increments the next stimulus level from the current level by 1 (step S304). If the determination result in step S302 is negative (No), the result can lead to the conclusion that the stimulus level by the stimulus signal is too low and the stimulus level applied to the trainee 2 is lower than the proper level in contrast to the case of step S304.

Next, the arithmetic processor 20 executes a process of determining whether or not a difference between an exercise speed detected with the exercise status detector 30 and a predetermined target movement speed is equal to or larger than a predetermined value (step S308). The predetermined target movement speed is a value determined by the "speed instructed in the training action instruction information" in the criterion 3 in the "training evaluation program." Specifically, evaluation of the speed may be, for example, evaluation of an average speed of an exercise of one unit, evaluation of a maximum speed or a minimum speed, or evaluation of the speed in a specific section of a certain exercise, the specific section being selectively extracted. The predetermined value (determination value) to be used for determination in this step is specified on the basis of whether or not the value is large enough to be used to determine that a difference from the target movement speed is significant, i.e., whether or not a difference from the target movement speed is in an allowable range.

When the determination result in step S308 is affirmative (Yes), then the arithmetic processor 20 executes a process of determining whether or not "difference from the target movement speed" detected in step S308 is beyond a set value with the target movement speed as a reference (step S310). In this step, it can be determined whether or not the movement speed of the exercise status detector 30 is too fast with the target movement speed as a reference.

When the determination result of step S310 is affirmative (Yes), the arithmetic processor 20 decrements a next stimulus level from the current level by 1 (step S312). If the determination result in step S310 is affirmative (Yes), the result can lead to the conclusion that the stimulus level by the stimulus signal is too high and the stimulus level applied to the trainee 2 is higher than the proper level.

If the determination result of step S310 is negative (No), the arithmetic processor 20 increments the next stimulus level from the current level by 1 (step S314). If the determination result in step S310 is negative (No), the result can lead to the conclusion that the stimulus level by the stimulus signal is too low and the stimulus level applied to the trainee 2 is lower than a proper level in contrast to the case of step S312.

Next, the arithmetic processor 20 executes a process of determining whether or not a difference between a grip value detected with the exercise status detector 30 and a predetermined target grip value is equal to or larger than a predetermined value (step S316). The predetermined target grip value is a value determined by the "grip value instructed in the training action instruction information" in the criterion 5 in the "training evaluation program." One piece of the "training action instruction information" may include this predetermined target grip value.

When the determination result in step S316 is positive (Yes), then the arithmetic processor 20 executes a process of determining whether or not the "difference from the target grip value" detected in step S316 is beyond a set value with the target grip value as a reference (step S318). In this step, it can be determined whether or not the grip is too strong (is beyond the target grip value) with the target grip value as a reference.

When the determination result of step S318 is affirmative (Yes), the arithmetic processor 20 decrements a next stimulus level from the current level by 1 (step S320). If the determination result in step S318 is affirmative (Yes), the result can lead to the conclusion that the stimulus level by the stimulus signal is too high and the stimulus level applied to the trainee 2 is higher than the proper level.

If the determination result of step S318 is negative (No), the arithmetic processor 20 increments the next stimulus level from the current level by 1 (step S322). If the determination result in step S318 is negative (No), the result can lead to the conclusion that the stimulus level by the stimulus signal is too low and the stimulus level applied to the trainee 2 is lower than the proper level in contrast to the case of step S320.

Then, the current routine is ended.

Through the steps S304, S306, S312, S314, S320, and S322, the value of the next stimulus level is incremented or decremented (added or subtracted). The value of the stimulus level obtained in the end can be used as a guideline for manual regulation of the stimulus signal generator 50 in the next training. Accordingly, the degree of adequacy of the stimulus signal can be evaluated with respect to each exercise type, and the sum total of the respective evaluation results can be calculated as a next stimulus level. The value of the next stimulus level may be increased or decreased not only by addition and subtraction but also by, for example, multiplication or division of a predetermined coefficient.

When the routine of FIG. 15 is ended, the process proceeds to step S122 in FIG. 14. In result output of step S122, the result is outputted by one of the following methods.

(1) The numerical value representing the next stimulus level itself is expressed with plus, zero, or minus, and is outputted to the output device 40 (for example, a monitor 42). The numerical value displayed herein may be a numerical value representing the next stimulus level calculated in accordance with the flowchart of FIG. 15.

(2) If the next stimulus level is a plus value, "too high" may be displayed, and if it is a minus value, "too low" may be displayed. Thus, whether the value of the next stimulus level should be set higher or lower or be in status quo may qualitatively be expressed. The result is outputted to the output device 40 (for example, the monitor 42).

(3) Output in the form of questionnaire. More specifically, if the value of the next stimulus level indicates that the stimulus signal is too strong, a message like "Is stimulus signal too strong?" is displayed. On the contrary, if the value of the next stimulus level indicates that the stimulus signal is too weak, a message like "Is stimulus signal too weak?" is displayed. This makes it possible to provide a guideline to be used in the case of manually regulating an operation unit 50*a* of the stimulus signal generator 50 and to encourage the trainer and the like and/or the trainee 2 to determine by themselves in the form of a questionnaire.

According to the result output by the above-described methods (1) to (3), the next stimulus level is displayed, which can encourage determination regarding what kinds of measure to be taken for the evaluation result. In other words, the trainer and the like and/or the trainee 2 themselves can make a final determination regarding whether the control value of the stimulus signal is maintained, incremented, or decremented.

In the second embodiment, "information relating to the stimulus signal" is stored in the database 22. The stored "information relating to the stimulus signal" is used for training evaluation.

However, the present invention is not limited to this configuration. It is not necessary to store the "information relating to the stimulus signal" in the database 22, and it is also not necessary to use the "information relating to the stimulus signal" for training evaluation. In that case, the stimulus signal generator 50 side and the arithmetic processor 20 side are configured to be completely separated. In other words, in the stimulus signal generator 50, the stimulus signal is suitably adjusted by hand. Meanwhile, since the operation of the device according to the above-described first embodiment is executed, the output signals from the sensor group (the pressure sensor 34, the various sensors portion 36, the position sensor 38) included in the exercise status detector 30, and the like may be used to perform the training evaluation.

(Program Recording Medium, Program, and Training Method)

In the present invention, the control process, the arithmetic process, the determination process, and other processes described in the above-stated first and second embodiments, as well as the processes in each flowchart illustrated in the drawings may be stored in CD-ROMs, DVD-ROMs, and other "program recording media", and be provided in these forms. The present invention may also be provided in the form of a "training device control program" and may be distributed as an independent program. The controls, the analyzing methods, and the contents of the processes performed in the above-described embodiments may be implemented as the aspects of the "training method."

REFERENCE SIGNS LIST

2 trainee
10 training device
20 arithmetic processor
22 database
25 input device
30 exercise status detector
30*a* exercise detection unit
32 body portion
33, 33*a*, 33*b* grip portion
34 pressure sensor
36 various sensors portion
38 position sensor
40 output device
42 monitor
44 speaker
50 stimulus signal generator
52 stimulus signal generator body
52*a* operation unit
54 electrode pad
56 stimulus signal generation unit
210 training device
256 stimulus signal generation unit

The invention claimed is:

1. A training device comprising:
an information outputter including at least one of a monitor and a speaker;
an exercise status detector including (i) a body portion, (ii) a first grip portion spaced apart from a second grip portion by the body portion, and (iii) sensors detecting movement of the exercise status detector, wherein the exercise status detector is shaped like a dumbbell, and wherein the exercise status detector includes the body portion as a shaft;
a processor and associated storage that (i) store training action instruction information, (ii) output the stored training action instruction information via the information outputter, and (iii) evaluate a degree of matching between a content of the training action instruction information and the movement of the exercise status detector based on output signals from the sensors; and
a stimulus signal generator communicatively coupled to the processor and capable of providing a stimulus signal to an arm of a trainee,
wherein the sensors of the exercise status detector include:
a plurality of pressure sensors, provided with each of the first grip portion and the second grip portion, that detect a grip or a finger pressure when those grip portions are gripped by the trainee;
an acceleration sensor detecting acceleration according to the movement of the body portion; and
an angle sensor detecting a rotation angle or a tilt angle of the body portion.

2. The training device according to claim 1, wherein the processor and associated storage store information relating to the stimulus signal of the stimulus signal generator, and calculate information relating to an adequacy degree of the stimulus signal based on (i) the output signals from the sensors of the exercise status detector, (ii) the content of the training action instruction information, and (iii) the information relating to the stimulus signal.

3. The training device according to claim 2, wherein the processor and associated storage calculate a next stimulus level as the information relating to the adequacy degree of the stimulus signal, and increase or decrease the next stimulus level based on the output signals from the sensors of the exercise status detector and a target value of exercise in the content of the training action instruction information.

4. The training device according to claim 3, wherein
the processor and associated memory inform, via the information outputter, of at least one of a result of evaluation with respect to the degree of matching and information relating to an operation of the stimulus signal generator, and the information relating to the operation of the stimulus signal generator is calculated based on the result of evaluation with respect to the degree of matching.

5. The training device according to claim 4, wherein the information relating to the operation of the stimulus signal generator includes information providing a guideline to be used in the case of manually regulating the stimulus signal generator.

6. The training device according to claim 1, wherein:
the processor and associated memory generate, based on a result of the evaluation of the degree of matching, signal specifying information to specify the stimulus signal to be generated by the stimulus signal generator, and transmit to the stimulus signal generator the signal specifying information, and
the stimulus signal generator generates the stimulus signal in accordance with the signal specifying information.

7. The training device according to claim 1, wherein the training action instruction information includes:
information to instruct a training action to move the exercise status detector,
information to instruct a training action to rotate or tilt the exercise status detector, and
information to instruct a training action to grip the exercise status detector.

8. The training device according to claim 1, wherein the training action instruction information includes information for instructing to perform a training action with the exercise status detector held by both arms while the stimulus signal of the stimulus signal generator is applied to one arm of the trainee.

9. The training device according to claim 1, wherein the evaluation of the degree of matching includes:
evaluation of a degree of matching between acceleration instructed in the training action instruction information and actual acceleration of movement of the exercise status detector, and
evaluation of a degree of matching between a grip value instructed in the training action instruction information and a grip value based on an output value from at least one of the plurality of pressure sensors.

* * * * *